US00PP23823P3

(12) United States Plant Patent
De Wit et al.

(10) Patent No.: US PP23,823 P3
(45) Date of Patent: Aug. 13, 2013

(54) APPLE TREE NAMED 'B3F45'

(50) Latin Name: *Malus domestica*
Varietal Denomination: B3F45

(75) Inventors: Inge De Wit, Lovenjoel (BE); Hendrik Eyssen, Holsbeek (BE); Johan Keulemans, Korbeek-Lo (BE); Johan Nicolaï, Sint-Truiden (BE); Els Pauwels, Amougies (BE); Paul Van Laer, Heks (BE)

(73) Assignee: Better3Fruit, N.V., Heverlee (BE)

( * ) Notice: Subject to any disclaimer, the term of this patent is extended or adjusted under 35 U.S.C. 154(b) by 436 days.

(21) Appl. No.: 12/926,542

(22) Filed: Nov. 24, 2010
(Under 37 CFR 1.47)

(65) Prior Publication Data

US 2011/0167527 P1 Jul. 7, 2011

(30) Foreign Application Priority Data

Nov. 26, 2009 (QZ) ..... PBR 2009/2504

(51) Int. Cl.
*A01H 5/00* (2006.01)

(52) U.S. Cl.
USPC ..... Plt./172

(58) Field of Classification Search
USPC ..... Plt./172, 161
See application file for complete search history.

*Primary Examiner* — Kent L Bell
(74) *Attorney, Agent, or Firm* — Foley & Lardner LLP

(57) ABSTRACT

A new and distinct *Malus domestica* apple tree variety named 'B3F45', particularly characterized by very firm flesh, long storability, long shelf life, very sweet taste and rough skin of fruit.

9 Drawing Sheets

Figure 1:
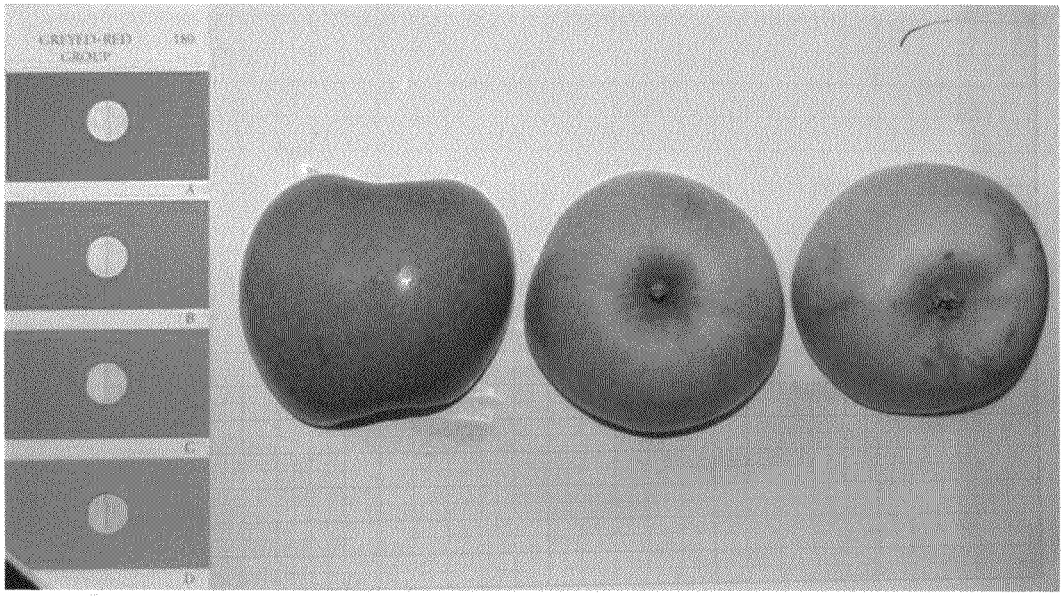

Latin name of the genus and species of the plant claimed: *Malus domestica.*

Variety denomination: 'B3F45'.

PRIORITY CLAIM

This application claims priority under 35 U.S.C. §119(f) of the European Community Plant Variety Rights No. 2009/2504 filed Nov. 26, 2009.

BACKGROUND OF THE INVENTION

The present invention relates to a new and distinct variety of Apple tree, botanically known as *Malus domestica* of the Rosaceae family, and hereinafter referred to by the variety denomination 'B3F45'.

The new *Malus* variety is a product of a controlled breeding program conducted by the inventors, Inge De Wit, Hendrik Eyssen, Johan Keulemans, Johan Nicolaï, Els Pauwels and Paul Van Laer, in Rillaar, Belgium. The objective of the breeding program was to develop a new *Malus* variety with crisp and juicy flesh, as well as good storage capacity and shelf life.

The new *Malus* variety originated from a cross made by the inventors in 1993 in Belgium. The female or seed parent is the *Malus domestica* variety designated 'Gala' (unpatented). The male or pollen parent is the *Malus domestica* variety designated 'Braeburn' (unpatented). The new *Malus* variety was discovered and selected by the inventors within the progeny of the stated cross in a controlled environment in Belgium.

Asexual reproduction of the new *Malus* variety by grafting was first performed Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'B3F45' which in combination distinguish this Apple tree as a new and distinct variety:

1. very firm flesh;
2. long storability;
3. long shelf life;
4. very sweet taste; and
5. rough skin of fruits.

In comparison to the parental varieties, 'GALA' (unpatented) and 'BRAEBURN' (unpatented), 'B3F45' differs primarily in the traits listed in Table 1.

TABLE 1

| Trait | New Variety 'B3F45' | Female Parent 'GALA' (unpatented) | Male Parent 'BRAEBURN' (unpatented) |
|---|---|---|---|
| fruit skin surface | rough skin | smooth skin | smooth skin |
| fruit over color | red | bright red | brown-red |
| fruit taste | sweet | sour-sweet to sweet | sour to sour-sweet |
| harvest time | late | early | late |
| storability | long | medium | long |

Of the many commercial varieties known to the present inventor(s), the most similar in comparison to the new *Malus* variety 'B3F45' is the *Malus* variety 'Fuji' (unpatented), in the following characteristics described in Table 2:

TABLE 2

| Characteristic | New Variety 'B3F45' | Comparison Variety 'FUJI' (unpatented) |
|---|---|---|
| tree habit | upright-spreading | spreading |
| fruit over color | red | brown-red |

BRIEF DESCRIPTION OF THE PHOTOGRAPHS

The accompanying photographs illustrate the overall appearance of the new *Malus* variety 'B3F45' showing the colors as true as is reasonably possible with colored reproductions of this type. Colors in the photographs may differ slightly from the color values cited in the detailed botanical description, which accurately describe the color of 'B3F45'.

FIG. 1—shows a close-up view (side, top and bottom) of mature fruit of 'B3F45'.

Figure 2:
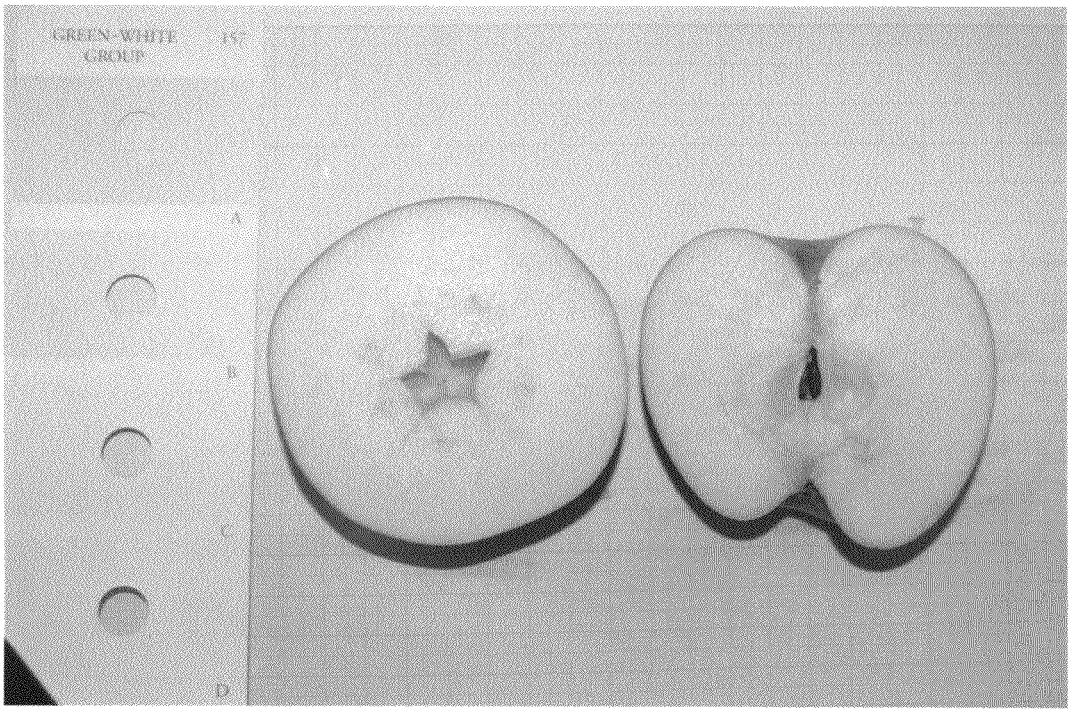

FIG. 2—shows dissection views of mature fruit of 'B3F45'.

Figure 3:
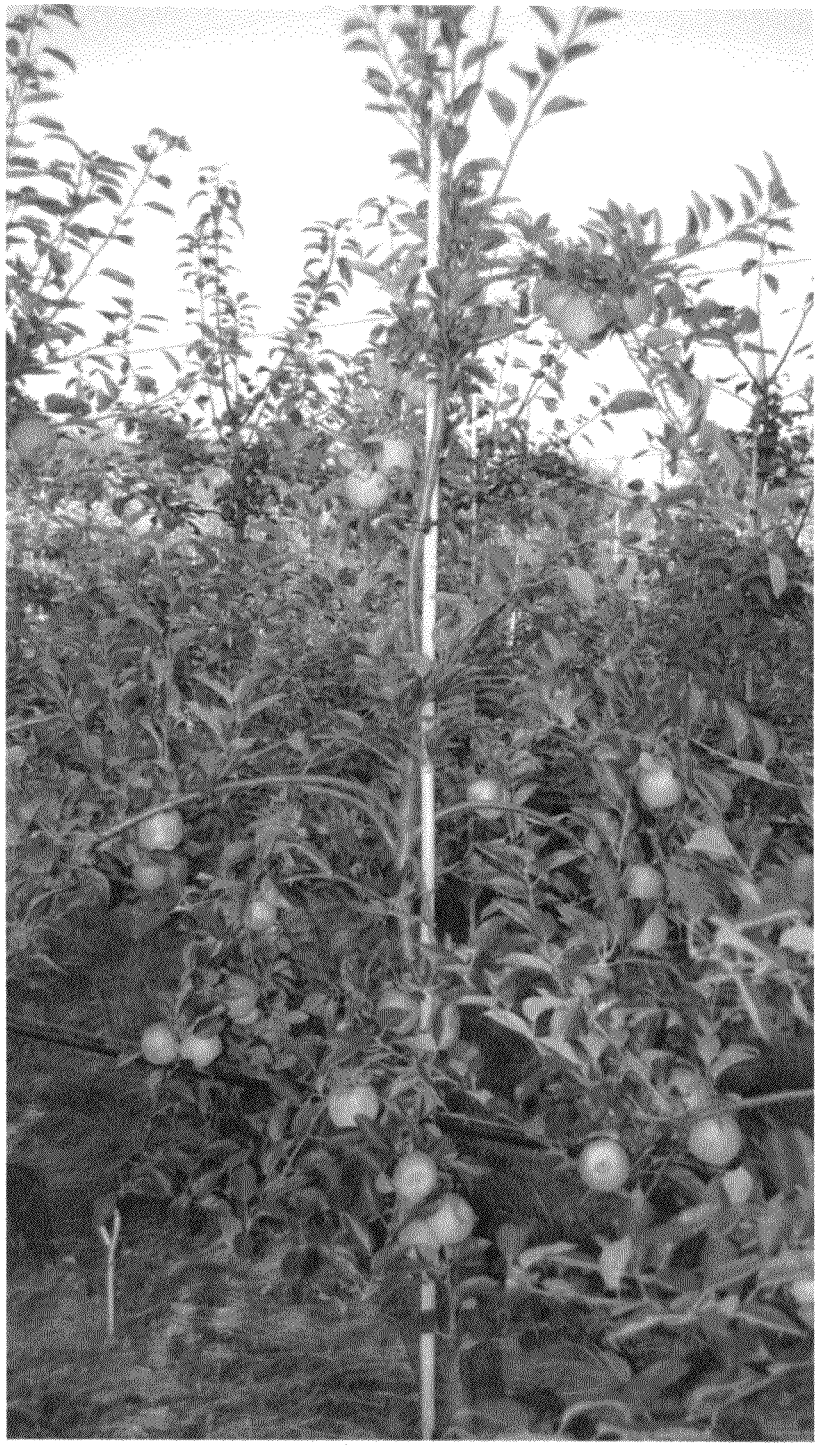

FIG. 3—shows a fruit-bearing tree of 'B3F45', at 4 years of age.

Figure 4:
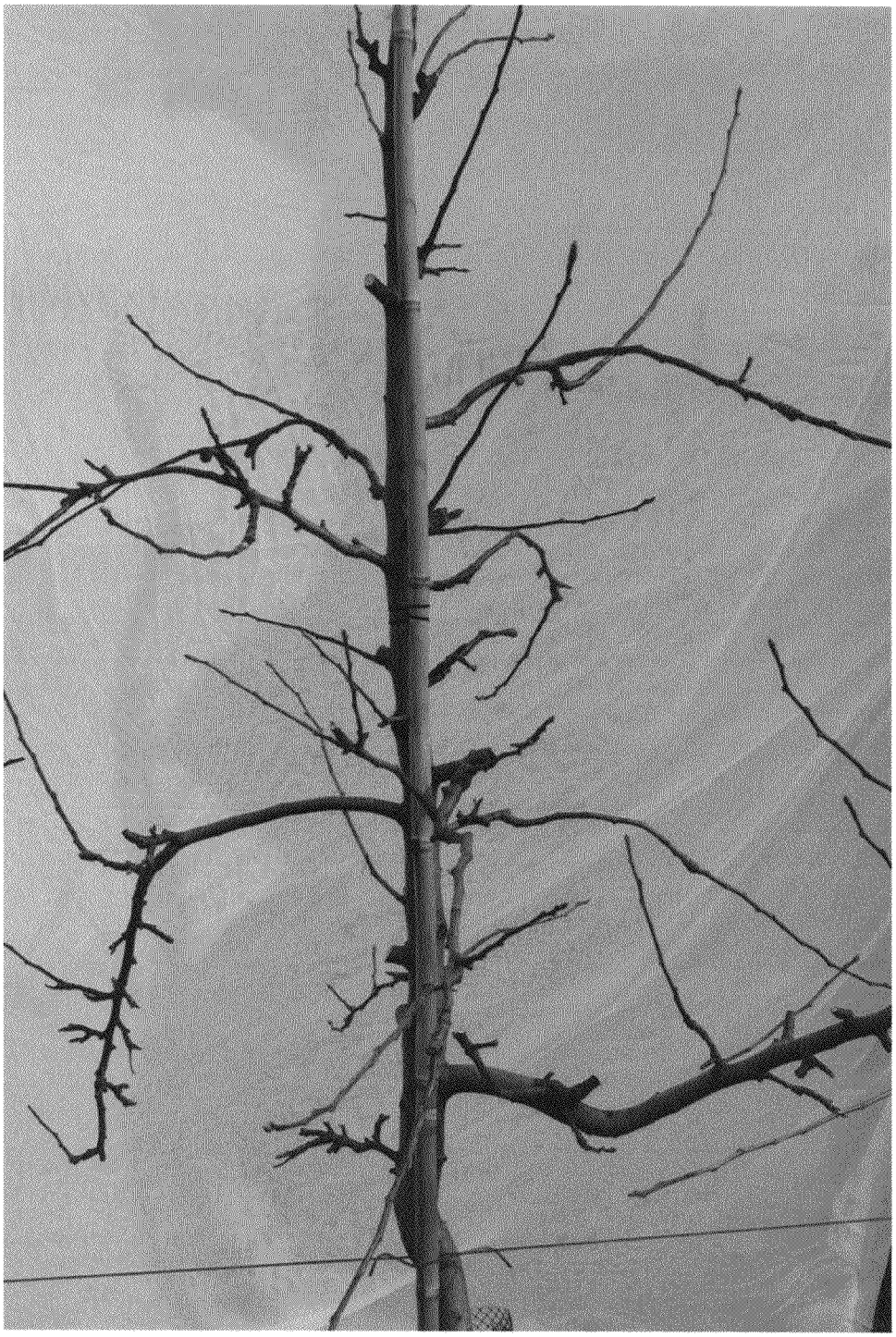

FIG. 4—shows a dormant tree of 'B3F45', at 9 years of age

Figure 5:
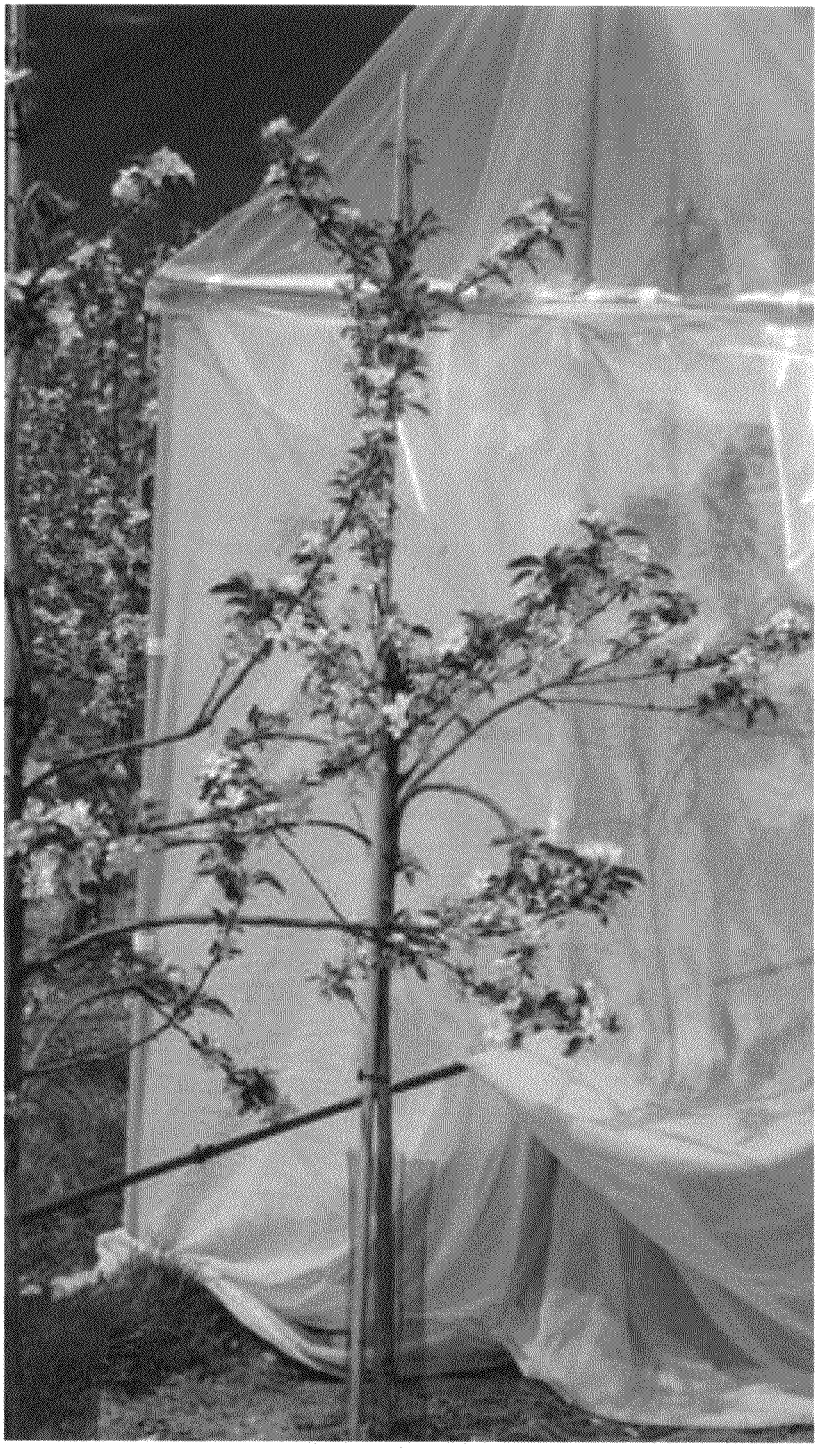

FIG. 5—shows a blooming tree of 'B3F45', at 4 years of age.

Figure 6:
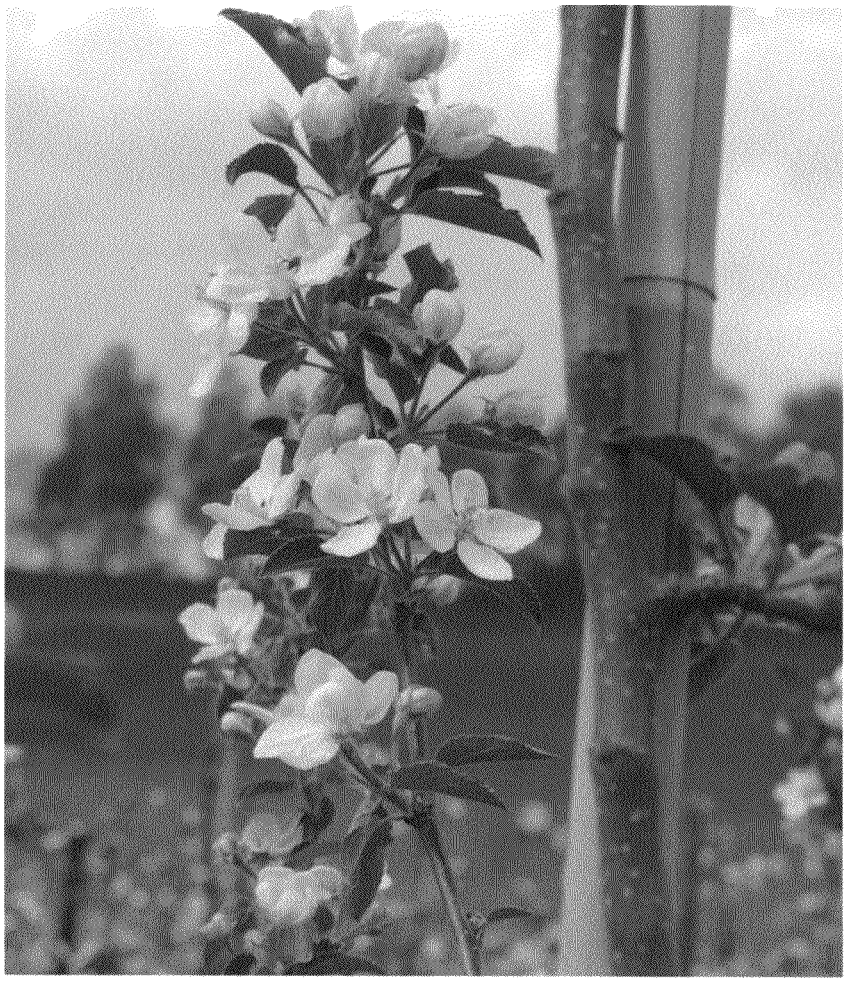

FIG. 6—shows inflorescence of 'B3F45'.

Figure 7:
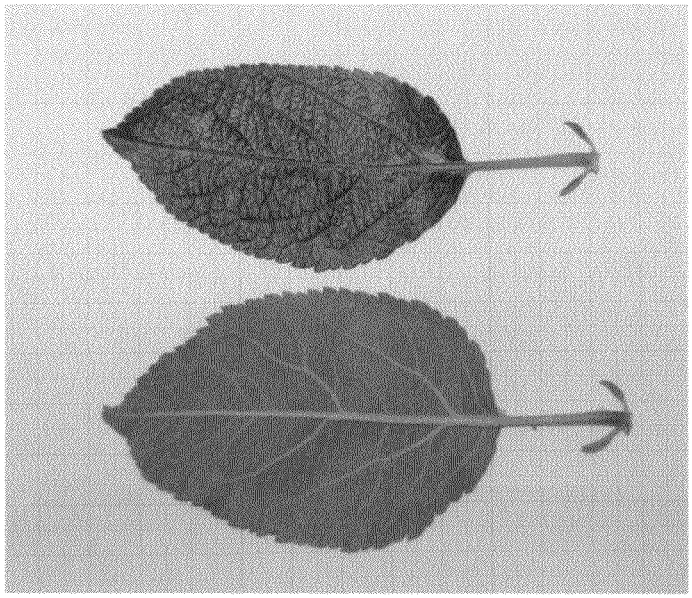

FIG. 7—shows top and bottom view of leaves of 'B3F45'.

Figure 8:
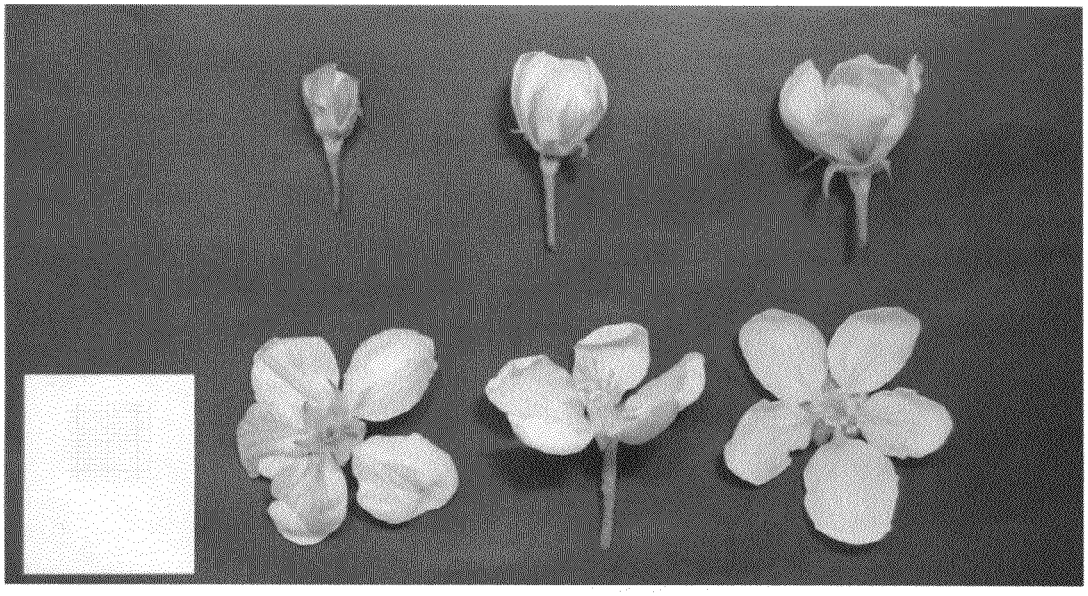

FIG. 8—shows different stages of development of the flowers and the bottom, side and top view of a fully expanded flower of 'B3F45'.

Figure 9:
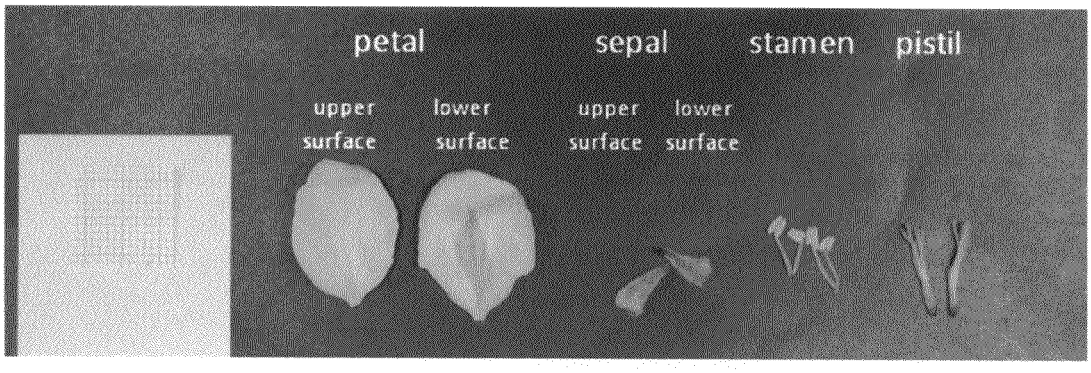

FIG. 9—shows different parts of a flower of 'B3F45'.

DETAILED BOTANICAL DESCRIPTION

The new *Malus* variety 'B3F45' has not been observed under all possible environmental conditions. The phenotype of the new variety may vary with variations in environment such as temperature, light intensity, and day length without any change in the genotype of the apple tree.

The aforementioned photographs, together with the following observations, measurements and values describe trees of 'B3F45' as grown in the orchard in Rillaar, Belgium, under conditions which closely approximate those generally used in commercial practice.

Unless otherwise stated, the detailed botanical description includes observations, measurements and values based on 4 year old 'B3F45' trees grown in the orchard in Rillaar, Belgium from 2009 to 2010. Quantified measurements are expressed as an average of measurements taken from a number of trees of 'B3F45'. The measurements of any individual tree, or any group of trees, of the new variety may vary from the stated average.

Color references are made to The Royal Horticultural Society Colour Chart (R.H.S.), (4th edition, 2001), except where general colors of ordinary significance are used. Color values were taken under daylight conditions at approximately 3:00 pm in Rillaar, Belgium.

All of the trees of 'B3F45', insofar as they have been observed, have been identical in all the characteristics described below.

Classification:

*Botanical.*—*Malus domestica.*

Parentage:

*Female or seed parent.*—*Malus* variety designated 'GALA' (unpatented).

*Male or pollen parent.*—*Malus* variety designated 'BRAEBURN' (unpatented).

Propagation: Grafting to rootstocks.

Growing conditions:

*Light intensities.*—Full sunlight.

*Temperature.*—During day, grown in range of 2° C. to 23° C., and during evening, grow in range of −5° C. to 13° C. (based on average month temperature).

Tree:

*Age.*—Observed trees were 4 years old.

*Vigor.*—Strong vigor.

*Form.*—Ramified — upright/spreading.

*Habit.*—A normal-sized tree with one trunk and about 13.2+/−1.3 leaders; main branches spreading; crown symmetrical.

*Branching habit.*—Main branches angle is 56.0°+/−14.6 with respect to trunk if allowed to grow naturally.

*Density.*—About 2200 trees per hectare.

*Cropping behavior.*—Average beginning production; normal productivity and regular flowering; no biennial bearing.

*Type of bearing.*—Long shoots and spurs.

*Production.*—About 10.8 kg/tree in 2010 .

*Size at maturity.*—Height: 275+/−9 cm. Spread: 165+/−34 cm.

*Trunk.*—Height (up to leaders): 86+/−9 cm. Diameter: 31+/−3.7 mm. Texture: slightly rough. Bark color: Primarily RHS greyed-green 197B, with underbark RHS greyed-orange 165A. Trunk lenticels: Length: 1.37+/−0.37 mm (in the direction of the trunk). Width: 3.63+/−1.36 mm (diagonal to the trunk direction). Color: RHS greyed-orange 163C. Density: 1.9+/−0.7 per $cm^2$.

*Branches.*—Number per tree: 19.0+/−2.3. Length: Varies due to shape of tree; maximum of 113.4+/−13.6 cm; minimum of 1.4+/−0.5 cm. Diameter (at 2 years): 12.04+/−2.34 mm. Surface texture: slightly rough. Pubescence: none. Color: Mature (after about 3 years old): RHS greyed-orange 166B. New Growth: RHS greyed-orange 166A. Internode length: 27.79+/−6.62 mm. Internode diameter: 9.94+/−1.84 mm. Branch lenticels: Length: 1.36+/−0.40 mm (in the direction of the branch). Width: 2.58+/−0.96 mm (diagonal to the branch direction). Color: RHS greyed-yellow 161B. Density: 3.4+/−2.1 per $cm^2$.

*Spur.*—Present: Yes, but few. Distance between each spur: On the 2 and 3 year old branches, the distance is 55.0+/−26.7 mm. Diameter of each spur: 5.95+/−1.61 mm. Number of fruit per spur: 1.0+/−0.3.

Foliage:

*Arrangement.*—Alternate, simple, petiolated.

*Lamina.*—Size: Length: 77.97+/−7.25 mm (fully expanded leaf). Width: 48.73+/−4.94 mm (fully expanded leaf). Length/width ratio: between 1.32 and 1.95. Overall Shape: ovate, petiolated. Base shape: rounded (obtuse). Apex shape: acute. Margin: bisserate. Texture: Upper surface: smooth, glabrous. Under surface: medium pubescence. Attitude in relation to shoot: outwards, slightly upwards. Color (mature leaves): Upper surface: RHS green 137A. Under surface: RHS green 138B. Color (immature leaves): Upper surface: RHS yellow-green 144B. Under surface: RHS green 143C.

*Venation*.—Type: pinnate venation from central vein to the leaf edge. Color: RHS green 138B.

*Petiole*.—Length: 26.7+/−1.6 mm. Diameter: 1.85+/−0.22 mm. Texture: high pubescence. Color: RHS green 143B (upper), RHS yellow-green 145C (lower), RHS red-purple 60C.

*Stipule*.—Arrangement: free standing. Length (distance of stipules from basal attachment of petiole): 7.54+/−2.07 mm. Width: 1.40+/−0.52 mm.

Inflorescence:

*Blooming time*.—Medium (similar to 'Gala' and 'Braeburn').

*Blooming period*.—About 1 week.

*Fragrance*.—Slight.

*Type*.—Corymb.

*Number of flowers per inflorescence*.—4.3+/−0.9.

*Inflorescence size*.—Diameter: 68.10+/−7.62 mm. Depth: 43.75+/−5.36 mm.

*Buds*.—Terminal Buds: Number per spur: about 1. Shape: pointy, triangular. Length: 7.93+/−1.26 mm. Width: 4.72+/−0.38 mm. Texture: high pubescence. Color: Apex RHS greyed-orange 166A, and base RHS greyed-orange 166B. Scales: Number: 6.4+/−1.0. Overall shape: triangular, double folded around bud. Apex shape: three points (middle point is the longest). Base shape: straight, fully grown together with base. Color: Upper: RHS greyed-orange 166A. Lower: RHS yellow-green N144C. Lateral Buds: Number per spur: about 0. Shape: pointy, triangular. Length: 5.53+/−0.66 mm. Width: 3.46+/−0.33 mm. Texture: medium to high pubescence. Color: Apex, RHS greyed-orange 166A, and base, RHS yellow-green N144C. Scales: Number: 5.2+/−0.8. Overall shape: triangular, double folded around bud. Apex shape: three points (middle point is the longest). Base shape: straight, fully grown together with base. Color: Upper: RHS greyed-orange 166A. Lower: RHS yellow-green N144C.

*Petals*.—Arrangement: free (full bloom). Number per flower: Five. Size: Length: 17.18+/−1.96 mm. Width: 10.66+/−1.17 mm. Length/width ratio: from 1.29 to 2.02. Overall shape: obovate. Apex shape: rounded. Base shape: acute. Texture (upper surface): smooth. Texture (lower surface): smooth. Margin: entire. Color (upper surface): from RHS red-purple 69C to RHS red-purple 69D. Color (lower surface): from RHS red-purple 69D to RHS red-purple 70C.

*Sepals*.—Number per flower: Five. Size: Length: 6.05+/−1.39 mm. Width: 3.33+/−0.56 mm. Length/width ratio: from 1.20 to 2.69. Overall shape: triangular. Apex shape: acuminate. Base shape: truncate. Texture (upper surface): smooth, hairy. Texture (lower surface): smooth, hairy. Margin: entire. Color (upper surface): Apex RHS greyed-orange 172B, and base RHS green 143C. Color (lower surface): Apex RHS greyed-orange 172B, and base, RHS green 143C.

*Pedicel*.—Length: 22.72+/−3.61 mm. Diameter: 1.07+/−0.17 mm. Texture: smooth, slightly hairy (white hairs). Color: RHS green 143C.

Fruit:

*Keeping quality*.—It can be stored in cold temperature conditions for minimum 9 months without loosing firmness and juiciness. It has a shelf life of minimum 3 weeks without loosing firmness and juiciness.

*Maturity when described*.—Ripe for eating.

*Maturity period after full bloom*.—About 24 weeks after full bloom.

*Date of first and last picking* (*harvest*).—About second and third week of October.

*Type*.—Pome.

*General shape*.—Globose.

*Average weight*.—225.5+/−50.9 g.

*Fruit size*.—Average height: 66.9+/−7.1 mm. Average diameter (at widest point): 77.2+/−6.2 mm. Position of maximum diameter: ½ of height. Height/thickness ratio: from 0.72 to 1.04.

*Stem*.—Length: 18.57+/−4.32 mm. Diameter: 3.1+/−0.85 mm. Color: from RHS yellow-green 146D to RHS greyed-red 181 B.

*Stalk cavity*.—Depth: 15.84+/−2.83 mm. Width: 34.48+/−4.74 mm.

*Eye basin*.—Depth: 8.81+/−2.32 mm. Width: 36.11+/−4.68 mm. Crowning at calyx end: moderate. Position of sepals: separate. Calyx tube: closed or slightly open.

*Skin*.—Thickness: thin. Texture: slightly rough. Bloom: slight bloom. Greasiness: absent. Firmness (at picking time): 8.5+/−1.2 kg/cm$^2$ (measured without removing the skin). Overcolor Color: RHS greyed-red 180B. Percentage of skin surface with overcolor color: About 50 to 75%. Pattern of overcolor: solid flush with weakly defined stripes. Intensity of overcolor: medium. Ground color: RHS yellow-green 145C. Skin Lenticels: Length: 1.28+/−0.38 mm. Width: 0.98+/−0.3 mm. Color: RHS greyed-yellow 161A. Density: 3.9+/−1.0 per cm$^2$.

*Flesh*.—Color: RHS green-white 157C. Texture: very firm, crisp and juicy. Aroma: medium. Eating quality: excellent. Sugar content (at picking time): 16.2+/−2.5 Brix. Acidity/Starch (at picking time): 8.3+/−1.0 g/l malic acid. Core: Symmetry of core: round. Distinctness of core lines: weak. Locules: Number (per fruit): 5. Length: 9.02+/−1.78 mm. Width: 3.81+/−1.04 mm. Form: triangular.

Seeds:

*Number per fruit*.—7.4+/−3.3.

*Number per locule*.—1.6+/−0.8.

*Shape*.—Teardrop form.

*Length*.—9.78+/−0.59 mm.

*Width*.—5.2+/−0.46 mm.

*Texture*.—Smooth.

*Color*.—From RHS greyed-orange 166A to RHS greyed-orange 174A.

Reproductive organs:

*Androecium*.—Stamen: Number per flower: 17.9+/−1.71. Length: 9.76+/−1.59 mm. Anther: Length: 2.56+/−0.27 mm. Color: RHS yellow 4C. Filaments: Length: 7.08+/−0.71 mm. Color: RHS green-white 157B. Pollen: Amount: moderate. Color: RHS green-yellow 1C. Pollination Requirements: cross pollination.

*Gynoecium*.—Pistils: Quantity: 5. Length: 12.13+/−0.80 mm. Color: RHS yellow-green 144C. Stigmas: Length: 0.52+/−0.15 mm. Width: 0.41+/−0.16 mm. Color: RHS yellow-green 144C. Ovary: Length: 5.39+/−0.75 mm. Width: 1.01+/−0.15 mm. Color: RHS yellow-green 144C.

Use: Fresh market.

Disease/pest resistance: No known resistance.

Disease/pest susceptibility: Medium susceptibility to scab (*Venturia inaequalis*).

Winter hardiness: Tolerant to temperatures down to minimum −10° C. without observed damage to wood and buds of dormant Apple trees.

Drought/heat tolerance: Tolerant to temperatures up to minimum 40° C., growth is limited by drought periods without irrigation.

Shipping/storage characteristics: Low sensitivity to bruising; good storability under ULO-conditions for minimum 12 months.

We claim:

1. A new and distinct *Malus domestica* apple tree named 'B3F45', as illustrated and described herein.

* * * * *